(12) United States Patent
Oh

(10) Patent No.: US 7,473,217 B2
(45) Date of Patent: Jan. 6, 2009

(54) METHOD OF TREATING BACK AND NECK PAIN

(76) Inventor: Choong-Youl Oh, 15503 - 76 Avenue, Edmonton, Alberta (CA) T5R 3A4

( * ) Notice: Subject to any disclaimer, the term of this patent is extended or adjusted under 35 U.S.C. 154(b) by 336 days.

(21) Appl. No.: 11/306,936

(22) Filed: Jan. 17, 2006

(65) Prior Publication Data
US 2006/0211959 A1  Sep. 21, 2006

Related U.S. Application Data

(60) Provisional application No. 60/594,176, filed on Mar. 16, 2005.

(51) Int. Cl.
A61N 2/06  (2006.01)
(52) U.S. Cl. .......................................................... 600/9
(58) Field of Classification Search ............... 600/9–15; 601/15; 128/897, 898
See application file for complete search history.

(56) References Cited

U.S. PATENT DOCUMENTS 6,421,560 B1 * 7/2002 Yoo ............................ 600/548
6,432,036 B1 * 8/2002 Kim ............................... 600/9
6,652,445 B1 * 11/2003 Woo ............................ 600/15
6,776,753 B1 * 8/2004 Holcomb ..................... 600/15

* cited by examiner

Primary Examiner—Samuel G Gilbert
(74) Attorney, Agent, or Firm—Bennett Jones LLP

(57) ABSTRACT

A method of treating pain or injury in close proximity to the vertebral column in a subject with acupressure and magnetic therapy comprising the steps of placing a first magnetic focus radiation pointer on the skin of the point superior to the central point of injury or pain and a second magnetic focus radiation pointer on the skin of the point inferior to the central point of injury or pain, holding the pointers in place for a sufficient period of time and affixing a magnet to the central point of pain or injury. A preferred embodiment comprises the step of placing the first magnetic focus radiation pointer on the skin on a third point inferior to the first point but superior to a second point while placing the second magnetic focus radiation pointer on a fourth point on the skin inferior to the second point. In another preferred embodiment, each of the central, first, second, third and fourth points overlay a vertebra.

11 Claims, 1 Drawing Sheet

METHOD OF TREATING BACK AND NECK PAIN

CROSS REFERENCE TO RELATED APPLICATIONS

This application claims the priority benefit of U.S. Provisional Application No. 60/594,176 filed on Mar. 16, 2005 entitled "Method of Treating Neck and Back Injury", the contents of which are incorporated herein by reference.

BACKGROUND OF THE INVENTION

The invention relates to a method of treating whiplash and lower back pain using acupressure and magnetic therapy.

Whiplash and back injuries are the most common injuries that people suffer from automobile and other accidents. These injuries are extremely painful and devastating, often limiting physical movements in daily life, yet there are not many effective ways to treat those who suffer from such injuries with conventional medicine.

As a result of the failure of conventional medicine to effectively treat certain medical conditions, there is a growing tendency to explore the paths of alternative medicine.

One of these alternative practices is the use of acupuncture, which is an ancient Chinese art of inserting fine needles under the surface of the skin into specific locations on the body to treat various ailments. The number of needles and their locations depends on the condition and its severity. Acupuncturists treat conditions by placing needles into various points associated with that condition.

In a similar manner to acupuncture, acupressure is a healing method involving the placing of pressure to various points on the body associated with a condition. However, in acupressure, the skin is not broken.

Another alternative practice is the use of magnetic therapy. Although it is not entirely clear how magnetic therapy works, it has been found to increase blood flow and therefore oxygen carrying capacity, to change the migration of calcium ions to or from the bone, to alter the pH balance of various body fluids, to alter hormone production from endocrine glands and to alter the enzymatic activity and other biochemical processes of the human body.

U.S. Pat. No. 6,432,036, to Kim, entitled DEVICE FOR MAGNETIC FOCUS RADIATION MEDICAL TREATMENT, describes a pair of acupressure devices, each having a support member that holds a magnet in contact with a tip, a hollow casing with an external thread that receives the support member and an adjustable cap having an internal thread to engage the external thread of the hollow casing and a tip hole for allowing the tip to pass through the cap. The pointers are sold under the trademark Acutouch™. A method of using the device, comprising turning the cap to expose the desired portion of acupressure tip and holding the two acupressure devices against two respective points on the skin of the person to be treated, is disclosed. However, specific methods of using the device for the treatment of specific ailments are not disclosed.

U.S. Pat. No. 6,783,504, to Xie, entitled METHOD OF ACUPUNCTURE AND MAGNETIC TREATMENT FOR WEIGHT LOSS, describes a method that includes the steps of placing acupuncture tips into specified portions of the human body, removing the tips, and placing magnets onto the same locations that the tips previously occupied. However, specific locations for, and the treatment of, ailments other then for obesity and diabetes are not disclosed.

Therefore, there is a need in the art for an improved method of treating soft tissue injuries involving the spine, including whiplash, lower back pain, or generally pain in a subject's back.

SUMMARY OF THE INVENTION

In general terms, the present invention provides a method comprising the steps of placing the tips from two separate magnetic focus radiation pointers into specified locations about the spine, removing the tips, and placing magnets at the locations that the tips previously occupied.

BRIEF DESCRIPTION OF THE DRAWINGS

In order to more fully describe embodiments of the present invention, reference is made to the accompanying drawings. These drawings are not to be considered limitations in the scope of the invention, but are merely illustrative.

DETAILED DESCRIPTION OF PREFERRED EMBODIMENTS

Figure 1:
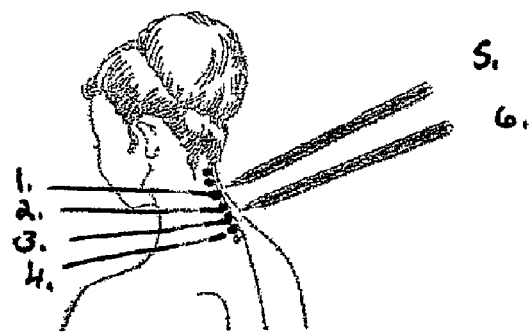
FIG. 1 is a perspective side view of a human upper spine.

The present invention provides a method of treating soft tissue injuries, and injuries of the lower and upper back and neck areas in particular.

The methods described herein require the use of a magnetic focus radiation device of the type described in U.S. Pat. No. 6,432,036, the contents of which are incorporated herein. In general, the devices comprise a support member holding both a magnet and a tip therein in a way such that the magnet comes into contact with the tip. This magnet is used for generating lines of magnetic force, while the tip is used for radiating the lines of magnetic force from the magnet onto a desired part of the human body. The tip is not intended to break the skin. Rather, it is quite blunt and is intended as an acupressure device.

In a preferred embodiment, the device comprises a hollow casing, having a predetermined length, which receives the support member therein. The tip projects from the lower end of the casing. This casing may have an external thread at its lower end. An outside plug detachably covers the top end of the casing and a cap is movably tightened to the external thread of the casing. This cap has an internal thread at its upper portion and movably engages with the external thread of the casing at the internal thread. The cap also has a tip hole at a central portion of its wall so as to allow the tip to pass through the tip hole. In the above device, the exposed length of the tip outside the cap is adjustable as desired by appropriately tightening or loosening the internally threaded cap relative to the externally threaded casing.

In an embodiment, the support member is an integrated body composed of upper, middle and lower parts, with a magnet holding part provided at the upper part and a tip holding part provided at the lower part while communicating with the magnet holding part. The upper and lower parts of the support member are tapered, with an annular step part being formed on the middle part at a position around a junction between the middle and lower parts, the support part also having a plurality of axial grooves extending on the external surface of the support part at positions covering the middle part and the annular step part. The axial grooves of the middle part communicate with the axial grooves of the annular step part while being leveled with each other at their bottom surfaces.

The support member is fitted into a coupling member at its upper and middle parts prior to being set within the casing, with both the annular step part of the support member being seated on the end of the coupling member and an inside cap detachably covering the top end of the coupling member. In the present invention, the coupling member is preferably made of aluminum.

The above support member and the cap are made of at least one material selected from the group consisting of an anion emitting material, a far infrared ray emitting material and a mixture thereof. A reflection tap, made of aluminum, is detachably fitted into the top end of the support member, with a gap being formed between the lower part of the support member and an internal surface of the casing, and so anions or far infrared rays emitted from the support member are reflected by the reflection tap and are radiated through both the axial grooves of the middle and annular step parts of the support member and the gap formed between the lower part of the support member and the internal surface of the casing.

In one example of the device, a first annular magnet may be set within the hollow casing at a position around the lower end of the casing. A second annular magnet is set within the cap at a position around the tip hole of the cap.

In an embodiment, at least one axial fitting channel is formed on the external surface of the casing by two parallel guide rails. One of the two parallel guide rails are projected inwardly along its top edge and a stop being formed at the lower end of the fitting channel.

The axial fitting channel of the casing axially selectively receives a first side edge of a connection plate therein, with a second side edge of the connection plate being fitted into the axial fitting channel of another casing, thus coupling two or more devices into a single system.

The support member is sectioned into a magnet support part and a tip support part, the magnet and tip support parts part being continued and integrated into a single body at a junction between them.

A suitable magnetic focus radiation device is commercially available under the trademark Genensen Acutouch™. Acutouch™ pointers are available in pairs, which are marked Red and Blue, but are not substantially different from each other, other than polarity. The Blue Acutouch™ pointer has a north magnetic field, while the Red pointer has a south magnetic field.

With reference to FIG. 1, for the treatment of a soft tissue injury to the neck and upper back, such as a whiplash-type injury, the patient is at a sitting position with head bent down. Assuming that point one 1, point two 2 and point three 3 are identified as injured or painful, the Red Acutouch™ pointer 5 is placed on point one 1 and the Blue Acutouch™ pointer 6 is placed on point three 3 and held for a sufficient period of time, which may vary but typically is about one minute. Points one 1, two 2, three 3 and four 4 are above consecutive vertebra. The pointers should be held perpendicular, that is, at a 90° angle, to the skin as illustrated in FIG. 1. The pressure of the pointer to the skin is preferably very slight. The pointers own weight is generally sufficient.

After a sufficient period of time has elapsed, reposition the pointers on the next lower vertebra. The Red Acutouch™ pointer 5 is placed on point two 2 and the Blue Acutouch™ pointer 6 is placed on point four 4 and held for one minute.

Figure 2:
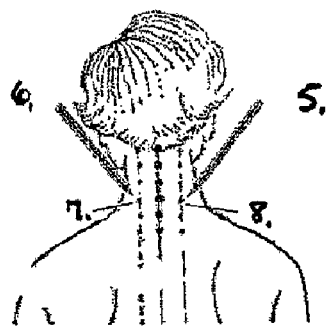
FIG. 2 is a front view of a human upper back.

With reference to FIG. 2, after the time has elapsed, the pointers are repositioned along lines that are 25 mm to the left 7 of the center of the spine and 25 mm to the right 8 of the center of the spine. The Red Acutouch™ pointer 5 is placed approximately 25 mm to the right of point one 1 and the Blue Acutouch™ pointer 6 is placed approximately 25 mm to the left of point one 1 and held for one minute.

After the time has elapsed the pointers are repositioned with respect to the next lower vertebra. The Red Acutouch™ pointer 5 is placed approximately 25 mm to the right of point two 2 and the Blue Acutouch™ pointer 6 is placed approximately 25 mm to the left of point two 2 and held for one minute.

After the time has elapsed the pointers are repositioned with respect to the next lower vertebra. The Red Acutouch™ pointer 5 is placed approximately 25 mm to the right of point three 3 and the Blue Acutouch™ pointer 6 is placed approximately 25 mm to the left of point three 3 and held for one minute.

After the time has elapsed the pointers are repositioned with respect to the next lower vertebra. The Red Acutouch™ pointer 5 is placed approximately 25 mm to the right of point four 4 and the Blue Acutouch™ pointer 6 is placed approximately 25 mm to the left of point four 4 and held for one minute.

After the time elapsed, small magnets are affixed to positions one 1, two 2 and three 3. The magnets should be placed with the north side against the skin. The magnets preferably have a strength of about 500 to 800 Gauss, and button shaped with a diameter of about 15 mm and a thickness of about 4 mm. The magnets may be affixed with adhesive tape.

Figure 3:
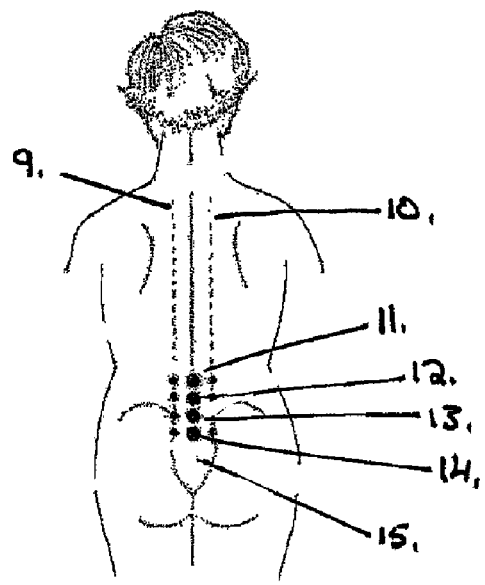
FIG. 3 is a front view of a human upper and lower back.

With reference to FIG. 3, for the treatment of lower back pain, the patient lies face down on bench. Assuming that point one 11, point two 12 and point three 13 are identified as injured or painful, the Red Acutouch™ pointer 5 is placed on point one 11 and the Blue Acutouch™ pointer 6 is placed on point three 13 and held for two minutes.

After the time has elapsed, reposition the pointers on the next lower vertebra. The Red Acutouch™ pointer 5 is placed on point two 12 and the Blue Acutouch™ pointer 6 is placed on point four 14 and held for two minutes. Point four is the upper end of the sacrum 15.

After the time has elapsed, reposition the pointers on the next lower vertebra. The Red Acutouch™ pointer 5 is placed on point three 13 and the Blue Acutouch™ pointer 6 is placed on point four 14 and held for two minutes.

With reference to FIG. 3, after the time has elapsed, the pointers are repositioned along lines that are 30 mm to the left 9 of the center of the spine and 30 mm to the right 10 of the center of the spine. The Red Acutouch™ pointer 5 is placed approximately 30 mm to the right of point one 11 and the Blue Acutouch™ pointer 6 is placed approximately 30 mm to the left of point one 11 and held for one minute.

After the time has elapsed the pointers are repositioned with respect to the next lower vertebra. The Red Acutouch™ pointer 5 is placed approximately 30 mm to the right of point two 12 and the Blue Acutouch™ pointer 6 is placed approximately 30 mm to the left of point two 12 and held for one minute.

After the time has elapsed the pointers are repositioned with respect to the next lower vertebra. The Red Acutouch™ pointer 5 is placed approximately 30 mm to the right of point three 13 and the Blue Acutouch™ pointer 6 is placed approximately 30 mm to the left of point three 13 and held for one minute.

After the time has elapsed the pointers are repositioned with respect to the next lower vertebra. The Red Acutouch™ pointer 5 is placed approximately 30 mm to the right of point four 14 and the Blue Acutouch™ pointer 6 is placed approximately 30 mm to the left of point four 14 and held for one minute.

After the time elapsed, magnets are affixed to positions one 11, two 12, three 13 and four 14. The magnets should be placed with the north side against the skin. The magnets are preferably, 500 to 800 Gauss, and button shaped with a diameter of 15 mm and a thickness of 4 mm. The magnets may be affixed with adhesive tape.

After treatment, examine the patient in standing position, feet about ten inches apart. Have the patient report any pain as he or she stretches backward slightly, bends forward slowly touching both hands on knees, and raising both hands to shoulder level to the sides and slowly turning the upper body to the left and to the right.

If a patient indicates a painful spot, mark the painful spot with a felt tip pen. Place the Red Acutouch™ pointer 5 at the painful spot and the Blue Acutouch™ pointer 6 at the point 30 mm away and towards the nearest vertebra and hold. Hold for one minute if the painful spot is on the upper back and hold one and half minutes if the painful spot is on the lower back. After the time has elapsed, place a magnet on the painful spot.

The inventor has developed an effective method to treat patients, borne out with good results. After the first treatment, almost all patients reported that there was no pain in the area that had been treated. Of those patients who had recent injuries (in the past one to three years), most have not had a need for a second treatment. About 40% of those who had been suffering from injuries over five to ten years before treatment returned for a second treatment one week after the first treatment. Only 10% of those who received a second treatment needed a third treatment two or three weeks later. Most of those patients who have received injuries over ten to thirty years ago have not needed more than three treatments.

What is claimed is:

1. A method for treating pain in close proximity to the vertebral column in a subject, comprising the steps of:
    a) identifying a central point of injury or pain;
    b) placing a first magnetic focus radiation pointer on the skin on a first point superior to the central point of pain while placing a second magnetic focus radiation pointer on the skin on a second point inferior to the point of pain, and holding the first and second pointers in position for a sufficient period of time;
    c) placing the first magnetic focus radiation pointer on the skin on a third point inferior to the first point but superior to second point while placing the second magnetic focus radiation pointer on a fourth point on the skin inferior to the second point, and holding the first and second pointers in position for a sufficient period of time;
    d) placing the first and second magnetic focus radiation pointers on the skin on points bilateral of at least one of the first, second, third and fourth points, and holding the pointers in position at each position of each bilateral pair for a sufficient period of time; and
    e) affixing a magnet on each of the first; second and third points, such that the North pole of the magnet is against the skin.

2. The method of claim 1 wherein at least one of the central point, first point, second point, third point, or fourth point overlie a vertebrae of the subject.

3. The method of claim 2 wherein each of the central point, first, second, third, and fourth points overlie vertebrae of the subject.

4. The method of claim 1 wherein steps (b), (c) and (d) are performed in the sequence identified in claim 1.

5. The method of claim 1 wherein each sufficient period of time is about one minute.

6. The method of claim 1 wherein each of the first to fourth spots are separated by a distance about equal to the distance between vertebrae in the subject.

7. The method of claim 6 wherein the bilateral points of step (d) are about 25 mm laterally away from the first, second, third or fourth points, as the case may be.

8. The method of claim 1 in which the magnetic focus radiation pointers are placed substantially perpendicular to the skin.

9. The method of claim 1 wherein the magnets are button magnets and are affixed to the skin with the north pole of the button magnet placed against the skin.

10. The method of claim 9 wherein the magnets are affixed with adhesive tape.

11. The method of claim 1 wherein the magnets have a strength of about 500-800 Gauss.

* * * * *